(12) United States Patent
Perlitz

(10) Patent No.: US 9,213,003 B2
(45) Date of Patent: Dec. 15, 2015

(54) METHOD FOR CHARACTERIZING A STRUCTURE ON A MASK AND DEVICE FOR CARRYING OUT SAID METHOD

(75) Inventor: Sascha Perlitz, Jena (DE)

(73) Assignee: Carl Zeiss SMS GmbH, Jena (DE)

( * ) Notice: Subject to any disclaimer, the term of this patent is extended or adjusted under 35 U.S.C. 154(b) by 169 days.

(21) Appl. No.: 13/995,250

(22) PCT Filed: Dec. 13, 2011

(86) PCT No.: PCT/EP2011/006278
§ 371 (c)(1),
(2), (4) Date: Jun. 18, 2013

(87) PCT Pub. No.: WO2012/084142
PCT Pub. Date: Jun. 28, 2012

(65) Prior Publication Data
US 2013/0308125 A1 Nov. 21, 2013

Related U.S. Application Data

(60) Provisional application No. 61/426,648, filed on Dec. 23, 2010.

(30) Foreign Application Priority Data

Dec. 23, 2010 (DE) .......................... 10 2010 056 407

(51) Int. Cl.
*G01N 21/956* (2006.01)
*G03F 1/84* (2012.01)
*G03F 7/20* (2006.01)

(52) U.S. Cl.
CPC ................ *G01N 21/956* (2013.01); *G03F 1/84* (2013.01); *G03F 7/70483* (2013.01)

(58) Field of Classification Search
CPC ...... G01N 21/956; G03F 1/84; G03F 7/70483
See application file for complete search history.

(56) References Cited

U.S. PATENT DOCUMENTS

| 3,879,131 A | 4/1975 | Cuthbert et al. |
| 4,200,396 A | 4/1980 | Kleinknecht et al. |

(Continued)

FOREIGN PATENT DOCUMENTS

| DE | 25 05 063 | 8/1975 | ............ G01M 11/00 |
| DE | 102008049365 | 4/2010 | ............ G02B 12/06 |

(Continued)

OTHER PUBLICATIONS

Japanese Office Action for Japanese Application No. 2013-545082 dated Jun. 2, 2014 (5 pages).

(Continued)

*Primary Examiner* — Michael A Lyons
*Assistant Examiner* — Violeta A Prieto
(74) *Attorney, Agent, or Firm* — Fish & Richardson P.C.

(57) ABSTRACT

A method is provided for characterizing a mask having a structure, comprising the steps of: —illuminating said mask under at least one illumination angle with monochromatic illuminating radiation, so as to produce a diffraction pattern of said structure that includes at least two maxima of adjacent diffraction orders, —capturing said diffraction pattern, —determining the intensities of the maxima of the adjacent diffraction orders, —determining an intensity quotient of the intensities. A mask inspection microscope for characterizing a mask in conjunction with the performance of the inventive method is also provided.

23 Claims, 6 Drawing Sheets

(56) References Cited

U.S. PATENT DOCUMENTS

| | | | |
|---|---|---|---|
| 4,303,341 A * | 12/1981 | Kleinknecht et al. | 356/636 |
| 4,408,884 A | 10/1983 | Kleinknecht et al. | |
| 6,466,315 B1 | 10/2002 | Karpol et al. | |
| 6,690,469 B1 * | 2/2004 | Shibata et al. | 356/369 |
| 7,280,230 B2 * | 10/2007 | Shchegrov et al. | 356/630 |
| 2001/0019407 A1 * | 9/2001 | Sato et al. | 356/237.4 |
| 2005/0062963 A1 | 3/2005 | Yoshida et al. | |
| 2005/0195414 A1 | 9/2005 | Rau et al. | |
| 2008/0055606 A1 | 3/2008 | Inoue et al. | |
| 2011/0101226 A1 | 5/2011 | Ben-Zvi et al. | |
| 2011/0164313 A1 | 7/2011 | Stroessner | |
| 2011/0188732 A1 | 8/2011 | Stroessner | |
| 2012/0075456 A1 * | 3/2012 | Seitz | 348/79 |
| 2012/0162755 A1 | 6/2012 | Stroessner et al. | |
| 2013/0321609 A1 * | 12/2013 | Seitz et al. | 348/79 |

FOREIGN PATENT DOCUMENTS

| | | | | |
|---|---|---|---|---|
| DE | 102009041405 | 3/2011 | | G02B 21/06 |
| JP | 8-146592 | 6/1996 | | G03F 1/08 |
| JP | 2001-159810 | 6/2001 | | G03F 1/08 |
| JP | 2002-116011 | 4/2002 | | G01B 11/24 |
| JP | 2005-049284 | 2/2005 | | G01B 11/02 |
| JP | 2005-091182 | 4/2005 | | G01N 21/956 |
| JP | 2008-009339 | 1/2008 | | G03F 1/08 |
| JP | 2008-216685 | 9/2008 | | G03F 1/08 |
| JP | 2009-163185 | 7/2009 | | G03F 1/08 |
| JP | 2010-533309 | 10/2010 | | G03F 1/08 |
| JP | 2011-517127 | 5/2011 | | H01L 21/027 |
| JP | 54-092286 | 3/2014 | | H05K 7/00 |
| WO | 2005/069082 | 7/2005 | | G03F 9/00 |
| WO | 2009/007977 | 1/2009 | | |
| WO | 2010/034433 | 4/2010 | | G03F 1/00 |

OTHER PUBLICATIONS

German Search Report for German Application No. 10 2010 056 407.9 dated Sep. 26, 2011 (5 pages).

H.P. Kleinknecht et al., "Linewidth Measurement on IC Masks and Wafers by Grating Test Patterns", *Applied Optics*, vol. 19, No. 4, pp. 525, 1980.

International Search Report for International Application No. PCT/EP2011/006278, Mar. 2, 2012.

* cited by examiner

METHOD FOR CHARACTERIZING A STRUCTURE ON A MASK AND DEVICE FOR CARRYING OUT SAID METHOD

CROSS-REFERENCE TO RELATED APPLICATIONS

This application is the National Stage of International Application PCT/EP2011/006278, filed on Dec. 13, 2011, which claims priority to German Application DE 10 2010 056 407.9, filed on Dec. 23, 2010, and U.S. Provisional Patent Application 61/426,648, filed on Dec. 23, 2010. The contents of the above applications are incorporated by reference in their entireties.

BACKGROUND

This patent specification is directed to a method for characterizing a structure on a mask.

This patent specification is also directed to a device for carrying out said method.

In the fabrication of semiconductor components, numerous measurement methods are used to monitor the results of the individual steps in the lithographic process. One fundamental task in this context is to measure the outer dimensions or shapes of the structures which are to be produced.

To check the quality of a process step, it is advantageous to examine the smallest imageable structures. These are referred to as the critical dimension, abbreviated CD. The critical dimension of a mask usually refers to the line width of a structure composed of alternating lines and spaces. In the lithographic process, this structure is first formed on a mask (photomask, reticle), for example in chromium on quartz glass. There are also other known masks, for example phase shift masks (PSM) or reflective masks, that are used particularly with short-wavelength illuminating radiation in the EUV range. By exposure in a scanner, this structure is imaged onto a wafer coated with resist. The desired structure is produced on the wafer by subsequent developing and etching.

The characterization of a structure, such as, for example, measurement of the CD or line width of a structure, can be performed both on the mask and on the wafer. On-wafer measurement does yield very meaningful data, since the final product is measured; it is very laborious, however, since the entire wafer exposure process has to be performed for the test.

If the characterization of a mask structure is performed on the mask itself, errors caused by the behavior of the mask during imaging and by other method steps are incorporated into the measurement. Errors on the mask are usually intensified by the scanner during imaging. Another problem is that the mask structures are known and are optimized by resolution enhancement technology (RET), and thus do not wholly match the structures that are to be imaged. This makes it difficult to measure the CD on the mask.

Both on mask and on wafer, CD measurement is performed by, for example, scanning electron microscopy (CD-SEM, critical dimension scanning electron microscopy).

Another option for characterizing masks is to analyze the aerial images of masks with a mask inspection microscope. In this method, the aerial image shows most of the features that are also projected onto the wafer.

Another option for characterizing masks and wafers is afforded by non-imaging optical methods. Various interrelated measurement methods are used for this purpose, such as, for example, conventional scatterometry, ellipsometry, diffractometry or reflectometry, known collectively under the generic term scatterometry. Masks can also be characterized by measuring mask transmission. The CD of a structure can also be determined by this method, as disclosed, for example, in EP 2171539 A1.

SUMMARY OF INVENTION

The object of the invention is to provide a fast and inexpensive method with high measurement accuracy and a device for characterizing a structure on a mask.

According to the invention, this object is achieved by means of a method for characterizing a mask having a structure, comprising the steps of: illuminating the mask with monochromatic illuminating radiation under at least one angle of illumination, so as to obtain a diffraction pattern of the structure that includes at least two maxima of adjacent diffraction orders; capturing the diffraction pattern; determining the intensities of the maxima of adjacent diffraction orders; determining an intensity quotient of the intensities.

This measure permits the rapid determination of an accurate measurement value for characterizing the structure of a mask. Since the quotient of the maxima of adjacent diffraction orders is calculated, variations in the intensity of the exposure strength have little or no effect on this method of measurement.

Determining the intensities of the diffraction order maxima from the captured diffraction patterns is a much simpler process than mask structure characterization based on aerial images of the mask structure. This reduces the computation time spent on image analysis by the data processing system used.

An additional advantage over the analysis of aerial images is that the characterization is averaged over the detail under examination.

If different diffraction maxima of different structures appear in the area under examination, however, the analysis can easily be limited to the two relevant diffraction maxima. The relevant diffraction orders can be determined in a simple manner by image processing.

In a further embodiment of the invention, the diffraction pattern is projected entirely onto a single detector for capture.

This measure has the advantage that a complete diffraction pattern is obtained quickly. Lateral movement of the detector is not necessary.

One advantage over the capture and analysis of aerial images is that the capture of diffraction patterns is much more tolerant of defocusing of the diffraction pattern. This makes it possible to perform a great many measurements at different positions on a mask without having to focus between individual measurements. This considerably increases the speed of characterization of a mask.

In a further embodiment of the invention, the diffraction pattern is being captured during a continuous relative movement between the mask and the detector.

In a version of this embodiment the continuous relative movement is accomplished by movement of the mask. In a further version of this embodiment the mask is placed on a mask holder to enable a continuous relative movement of the mask. The mask will e. g. moved in a plane parallel to the plane of the detector.

In a version of this embodiment the speed of movements and the exposure time of the detector is specified in a way that each portion of the region to be characterized contributes to the final diffraction pattern to the same extend.

This measure has the advantage that a fast characterization of a whole mask or of a large connected part of a mask is possible. Scanning of masks by capturing aerial images of the mask structure is more complex. Therefore single aerial images of the mask structure in sections have to be captured. But this requests short exposure times or slow scanning speeds. Alternatively more sophisticated detectors could be used, that allow a time delayed integration of the signals. So called TDI (time delayed integration)-detectors are used. Performing these methods charges of the detector are moved synchronously with the scanning movement to accomplish a long exposure time.

In a further embodiment of the invention, a line width of the structure is determined from at least one correlation between at least one determined intensity quotient of a structure and a known line width of that structure.

This measure has the advantage that absolute values can be accessed in a simple manner. The calibration can be performed against measurements of the structure on the mask or on the exposed wafer or against an aerial image of the mask.

In a further embodiment of the invention, the illuminating radiation produces on the mask an illumination field having a main region and an edge region, said edge region surrounding said main region, wherein the intensity of the illuminating radiation is constant in the main region but decreases continuously in the edge region.

This measure has the advantage of reducing the dependence of the determined intensity quotient on changes in the position of the to-be-characterized mask structure in the illumination field.

Mask inspection microscopes known from the prior art employ an illumination field that has a constant intensity distribution over the entire region, with the intensity decreasing almost abruptly to zero at the edge of this illumination field. Such intensity distributions are known as "top hat profiles."

A disadvantage associated with the use of these intensity distributions is that the determined intensity quotients of a structure can depend on the position of that structure in the illumination field. For example, in the case of a structure configured as "lines and spaces," of the kind mentioned at the beginning hereof, the parts of the structure in the illumination field that contribute to the diffraction of the illuminating radiation vary. This variation would depend on the position of the structure in the illumination field along the grating period of the structure. This variation causes a change in the determined intensity quotients. This leads to problems in the comparison of identical types of structures that are expected to yield identical intensity quotients. The reproducibility of the positioning of structures in the illumination field is limited. For the above reasons, positioning errors can cause errors in the intensity quotients that are to be determined.

In a further embodiment of the invention, the decrease in intensity in the edge region corresponds to a Gaussian function.

This measure has the advantage that the dependence of the intensity quotients on variations in the position of the mask structure in the illumination field is especially low.

In a further embodiment of the invention, the illumination field on the mask is defined by means of a field stop and the intensity distribution of the illumination field is adjusted by defocusing the field stop.

This measure has the advantage that a desired intensity distribution of the illumination field can be specified in a simple manner. The intensity distribution obtained by defocusing the field stop corresponds to that of the above-cited measure, in which the intensity of the illuminating radiation is constant in the main region of the illumination field, but decreases as a Gaussian function in the edge region.

In a further embodiment of the invention, the at least one illumination angle is adjusted to a grating period of the structure.

In this case, the illumination angle is adjusted in the direction of the normal to the surface of the mask, the z-axis, and/or in the direction of the surface of the mask, i.e., the azimuth angle.

This measure has the advantage that the diffraction maxima of the to-be-examined structures, to which the at least one illumination angle has been adjusted, are particularly sharply defined in the diffraction pattern. Adjusting the illumination angle has the effect that the diffraction orders to be analyzed are captured with the highest possible intensity or contrast, largely without any interference effects from other structures. This permits simple and precise analysis of the diffraction pattern.

In a further embodiment of the invention, the at least one illumination angle is adjusted to an orientation of the grating period of the structure on the mask.

In this measure, the illumination angle is adjusted in the direction of the surface, to the azimuth angle of the illuminating radiation. The surface of the mask is described by a right-angle coordinate system having an x- and a y-axis. For example, structures whose grating periods extend in the x- or y-direction can be disposed on masks. These structures are configured as lines and spaces, for example. If the grating period of a structure on a mask extends in the direction of the x-axis, then the structure is designated an x-structure. If the grating period extends in the direction of the y-axis, then the structure is designated a y-structure. The azimuth angle of the illuminating radiation is 0° in the case of x-structures and 90° in the case of y-structures.

Comparing the intensity quotients of different positions on a mask is especially meaningful for characterization when measurements of comparable structures, i.e., structures having the same nominal grating period and line width, are compared with one another. For instance, x- and y-structures having the same grating period and line width are an example of comparable structures.

This measure has the advantage that adjusting the illumination angle to the structures makes it possible to image the diffraction maxima of comparable structures with the highest possible contrast.

Since possible positions of the diffraction maxima in a captured diffraction pattern are specified by means of the at least one adjusted illumination angle, the analysis is further simplified.

In a further embodiment of the invention, the structure on the mask is illuminated simultaneously under at least two illumination angles, each of the illumination angles being adjusted to the orientation of the respective grating periods of different structures on the mask.

This measure has the advantage that structures having at least two orientations can be captured simultaneously. In this case, for example, the above-mentioned x- and y-structures present on masks can be examined together. This eliminates the need to change the illumination direction between measurements of x- or y-structures.

In a further embodiment of the invention, the at least one illumination angle is predefined by arranging a stop in a pupil plane of an illumination beam path.

This measure has the advantage that the illumination angle can be specified in a simple manner. The stops of a mask inspection microscope can be changed quickly and easily. The shape of the stop can be manipulated to yield almost any arbitrary illumination angle distribution.

This measure also has the advantage that an imaging method employing a mask inspection microscope can be used in rapid alternation with the capture of diffraction patterns. Thus, for example, both the diffraction pattern and the aerial image of a structure on a mask can be captured and analyzed.

In a further embodiment of the invention, the stop is configured as an annulus that is adjusted to the grating periods of different structures on the mask.

This measure has the advantage that optimal illumination angles can be specified for structures within a grating period or corresponding region, regardless of the orientation of the grating period on the mask.

In a further embodiment of the invention, the stop is configured as a monopole, the position of the pole being adapted to the orientation of the grating period of a structure on the mask.

This measure has the advantage that an optimum illumination angle can be specified for structures within a grating period or corresponding region and having a corresponding orientation of the grating period on the mask. In this case, for example, the above-cited x- or y-structures can be examined individually.

In a further embodiment of the invention, the stop is configured as an asymmetric dipole, the positions of the two poles being adapted to the orientations of the grating periods of different structures on the mask.

This measure has the advantage that the simultaneous illumination of the structure of the mask at two angles of illumination, as noted in connection with a previously cited exemplary embodiment, is easy to realize.

In a further embodiment of the invention, the intensities of the adjacent diffraction orders are normalized to a reference value, particularly to the intensity, measured during the characterization of a mask with no structure.

This measure has the advantage that the normalized intensities of the maxima of identical diffraction orders are comparable. This makes possible a further characterization of the structure on the mask. By analyzing the normalized intensities of the diffraction maxima, comparable structures can be identified in the diffraction pattern. In addition, comparing the normalized intensities of the diffraction maxima of different diffraction patterns furnishes a criterion for determining diffraction patterns of comparable structures.

In a further embodiment of the invention, the assignment of the maxima of two adjacent diffraction orders of a diffraction pattern to a structure is performed by applying at least one of the criteria: position of the diffraction order maxima, distance between the diffraction order maxima, intensities of the diffraction order maxima, spread of the diffraction order maxima.

This measure has the advantage that a further characterization of the structures can be done quickly and easily on the basis of the diffraction patterns. For example, it becomes possible to assign the maxima of two adjacent diffraction orders in a diffraction pattern to a structure. For example, lines and spaces of a specific grating period and line width can be detected.

In another embodiment of the invention, a further characterization of the structure is performed by comparing the captured diffraction pattern to a simulated diffraction pattern.

The diffraction pattern of the structure to be characterized can be simulated to the extent that the design of the mask is known. Deviations of the captured diffraction pattern from the simulated one are evidence of deviations of the structure on the mask from the structure specified in the design.

This measure has the advantage that the captured diffraction pattern can also be used to perform a comparison with the specified structure of the mask.

In a further embodiment of the invention, plural positions on the mask at which structures are characterized are specified.

This measure has the advantage that masks can be characterized rapidly.

In a further embodiment of the invention, plural positions evenly distributed over the surface of the mask are specified.

This measure has the advantage that masks can be characterized even when the available information on the structures is nonexistent or incomplete. This embodiment is particularly advantageous in combination with the cited embodiments for locating comparable structures.

In a further embodiment of the invention, comparable structures are identified in the diffraction patterns by applying at least one of the criteria: position of the diffraction order maxima, distance between the diffraction order maxima, intensities of the diffraction order maxima, spread of the diffraction order maxima, differences from simulated diffraction patterns.

This measure has the advantage that comparable structures can be located in a simple manner.

In a further embodiment of the invention, positions at which comparable structures are formed on the mask are specified.

This measure has the advantage that comparable structures can be selectively chosen. This eliminates unnecessary measurements and the need to select diffraction patterns of comparable structures from a large number of captured images. The specification of positions can be carried out particularly on the basis of the mask design.

In a further embodiment of the invention, the mean of the intensity quotients of all comparable structures and the percentage deviation of the individual intensity quotients from the mean are calculated.

This measure has the advantage that simple and meaningful assessment of the mask becomes possible. Given the usually small deviations of the line widths from the nominal value, the values obtained correspond in good approximation to the deviations of the critical dimension (CD) from the nominal value.

The invention also encompasses a mask inspection microscope comprising a data processing system that performs the steps of the method according to the invention.

The data processing system is, for example, a commercially available computer programmed in such a way that all the aforesaid methods and their embodiments can be carried out.

It is understood that the features of the invention cited above and explained in more detail below can be used not only in the described combinations, but also in other ones, without departing from the scope of the present invention.

BRIEF DESCRIPTION OF DRAWINGS

The invention will be described and explained in more detail below on the basis of a few selected exemplary embodiments and by reference to the drawings.

Therein, the figures illustrate.

DETAILED DESCRIPTION OF THE INVENTION

Figure 1:
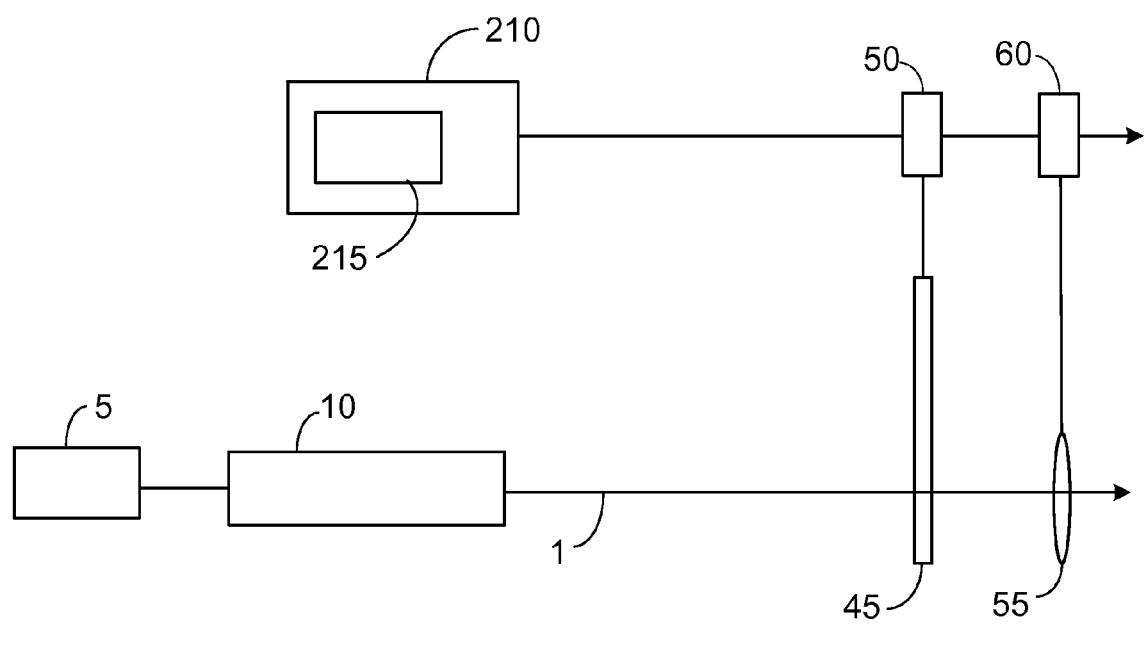
FIG. 1: a longitudinal section of a segment of an illumination beam path of a mask inspection microscope according to the invention.

A mask inspection microscope according to a first exemplary embodiment consists, as illustrated in FIG. 1, of a radiation source 5, an excimer laser, emitting illuminating radiation with a wavelength of 193 nm. This is followed along the optical axis 1 by a homogenizer 10, for homogenizing the intensity distribution of the illuminating radiation in the pupil plane and for the depolarization thereof.

Next comes the stop plate 45, which is disposed in a pupil plane of the illumination beam path 3. Control is effected via drive 50, which makes it possible to position the stops 51 precisely.

Figure 2:
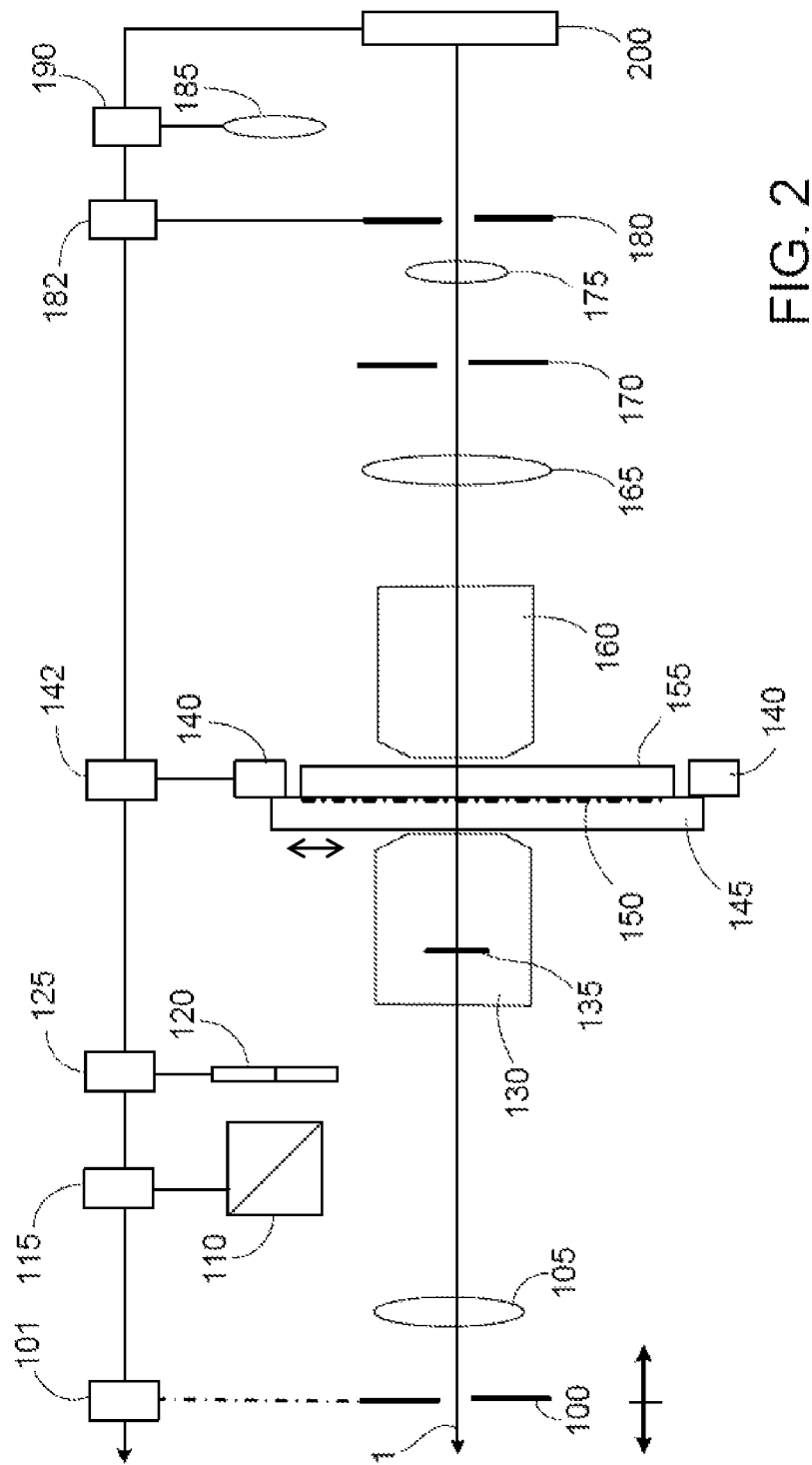
FIG. 2: a longitudinal section of a segment of an illumination beam path and imaging beam path of a mask inspection microscope according to the invention.
Figure 4:
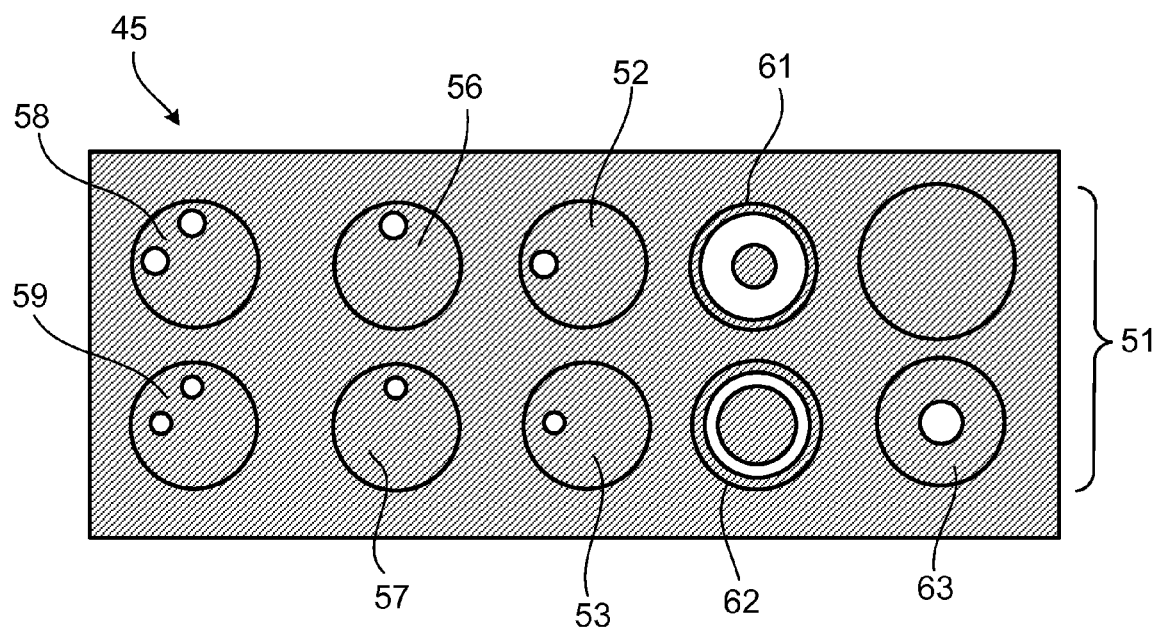
FIG. 4: a plan view of a stop plate with various stops.

The selected stop of stops 51 is projected in the desired size onto the pupil plane 135 of the condenser 130 by means of a zoom lens 55 equipped with an adjusting drive 60, as illustrated in FIG. 2. The imaging scale can be varied by a factor of 3. A stop plate is depicted in FIG. 4; the regions opaque to illuminating radiation are illustrated as shaded. If the stops are configured as reflective stops, the shaded regions are not reflective to illuminating radiation. The stop plate 45 is removably connected to the drive 50.

The continuation of the illumination beam path 3 from the first exemplary embodiment is illustrated in FIG. 2. The next element is a field stop 100 for defining the size and intensity distribution of the illumination field 240, which is sketched in FIG. 5, on the mask 145. Stop 100 is imaged onto the mask. A drive 101 serves to focus and defocus the image of the stop 100 on the mask.

The square opening of the field stop 100 has an edge length of 340 μm. After focusing on the mask, this yields an illumination field with an edge length of 26 μm. The use of different-sized field stops is provided for. In another variant not illustrated in the figures, no field stop 100 is used.

Figure 5:
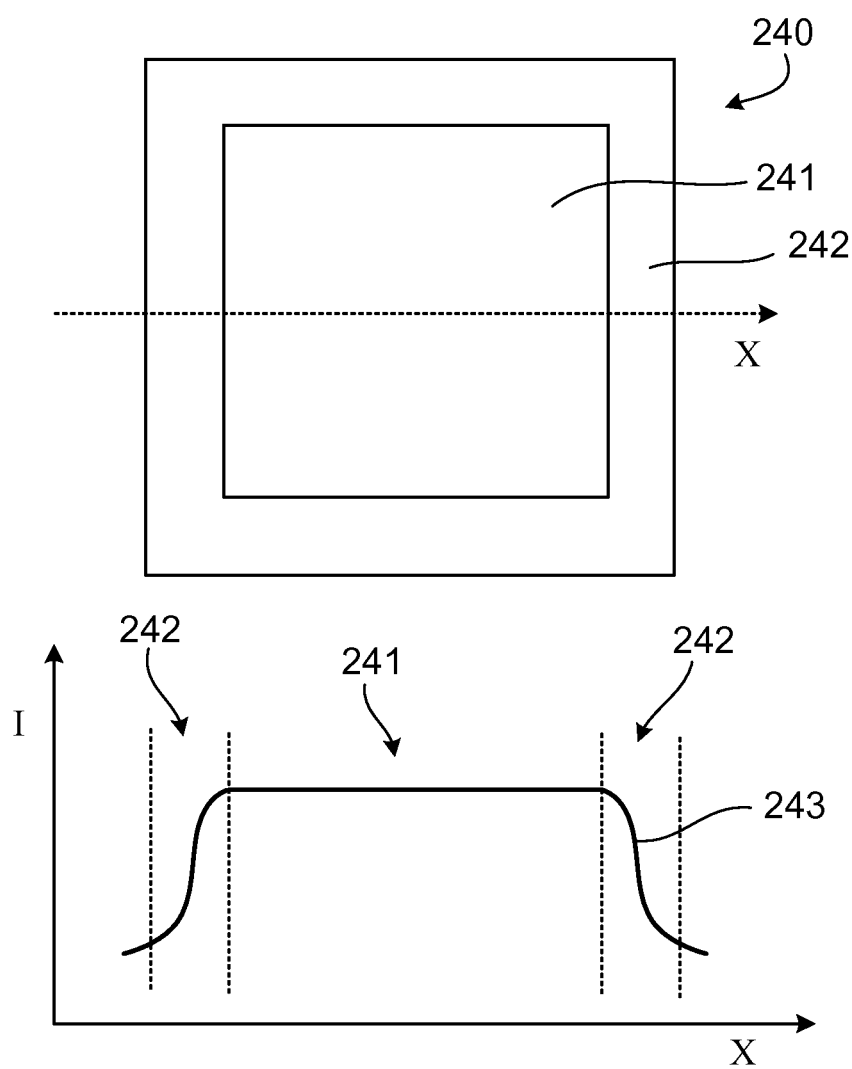
FIG. 5: the intensity distribution of an illumination field.

An example of a selectable illumination field 240 is sketched in FIG. 5. The intensity distribution of the illuminating radiation within the square illumination field 240 is constant within a square main region 241. The main region 241 is smaller than the illumination field 240 as a whole, and is surrounded by an edge region 242 of constant width. In the edge region, the intensity of the illuminating radiation decreases continuously to the edge of the illuminating field. The decrease in intensity can be described in the form of a Gaussian curve. The intensity distribution of the illuminating field 240 is plotted as a curve 243 along an axis denoted x. The x-axis bisects the illumination field 240 parallel to two opposite outer edges.

The field stop 100 is followed by a tube lens 105 and the condenser 130, which has a pupil plane 135.

To polarize the illuminating radiation, the polarizers 110 and 120 can be brought into the illumination beam path 3 by means of the drives 115 and 125. Polarizer 110 polarizes the illuminating radiation linearly; the direction of polarization can be adjusted by rotating the polarizer 110 by means of drive 115. To achieve tangential polarization of the illuminating radiation, polarizer 120, which is configured as a segmented polarization converter, is brought into the illumination beam path 3 in addition to polarizer 110. The linear polarization is rotated in sectors by this polarizer 120, thus resulting in approximately tangential polarization. Three variants of polarizer 120 are available (not shown in FIG. 2). Division into 4, 8 or 12 sectors can be chosen.

The mask 145 to be inspected, with the structure 150, is protected by a pellicle 155. The mask rests on the mask holder 140, which is moved by means of drive 142 laterally in a plane, denoted the xy plane, in order to move the mask to the desired position such that the location to be inspected is in the illumination beam path 3. Via drive 142, the mask is also moved for focusing purposes in the direction of the optical axis, the z-axis. The image of the mask is projected by objective 160 via tube lens 165, field stop 170, magnification optic 175 to the detector 200, a CCD (charged coupled device) chip. The numerical aperture is adjusted by means of the NA stop 180 with drive 182.

To image the pupil plane of the illumination beam path 3 onto the detector 200, a Bertrand lens 185 is brought into the illumination beam path 3 by means of drive 190.

All the drives 50, 60, 101, 115, 125, 142, 182, 190 and the detector 200 are connected to a data processing system 210 comprising an input/output unit 215. Control of the mask inspection microscope is effected through this data processing system 210. The particular image is stored by reading out of the detector 200; the image data are processed further.

In another exemplary embodiment not shown in the drawings, the mask inspection microscope operates in reflection. Here, the mask 145 is illuminated from the side of the structure 150. The mask thus lies precisely with its opposite side on the mask holder 140. The radiation reflected from the structure 150 is uncoupled from the illumination beam path 3 in a known manner by means of a beam splitter and continues on, as illustrated in FIG. 2, until it is imaged onto a detector 200.

Figure 3:
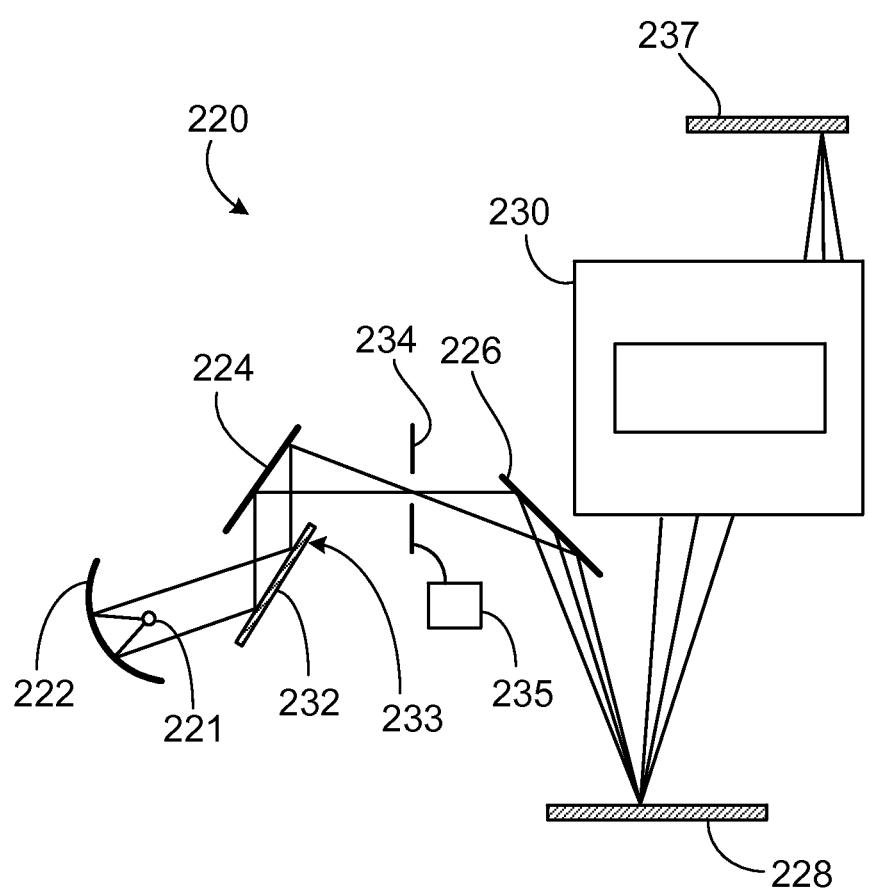
FIG. 3: a schematic representation of a mask inspection microscope according to the invention employing illuminating radiation in the EUV range.

In a further exemplary embodiment, the mask inspection microscope is operated with illumination radiation in the EUV range having a wavelength of 13.5 nm. The layout is depicted in FIG. 3. The radiation from an EUV radiation source 221 is gathered by a collector 222 and reflected via mirrors 224 and 226 to an EUV mask 228 that is to be examined. A field stop 234 serves to determine the size of the illumination field on the EUV mask 228. Stop 234 is imaged onto the mask. A drive 235 serves for focus or defocus the image of the stop 234. Stop 232, is disposed on a stop plate 233, is used to obtain the desired angle of illumination (analogously to, for example, the stops on the stop plate 45). An image of the EUV mask is projected via the imaging system 230 onto a detector 237, which, like drive 235, is connected to a not illustrated data processing system, which reads out the detector and processes the image data further. To image the pupil plane onto the detector 237, an additional mirror (not shown) is brought into the beam path.

Every location on the pupil plane corresponds to radiation of one angle from the object plane or the image field plane. Angles, such as illumination angles or diffraction angles, for example, are henceforth stated as corresponding locations on the pupil plane. The locations are given in polar coordinates, the pole being the center of the pupil. The radial coordinates are given in numerical aperture units. The polar axis is on an x-axis, the positive direction in the direction of illumination being defined as to the right. The x-axis and the orthogonal y-axis intersect with the center of the pupil plane. The azimuth angle is the angle between the radius and the x-axis.

The capture of a diffraction pattern is carried out as follows. The mask 145 comprising the structure 150 to be examined is placed in the mask inspection microscope on the mask holder 140. By means of drive 142, the desired slice of the structure 150 is brought into the beam path of the mask inspection microscope under control exerted by means of the data processing system 210. The Bertrand lens 185 is disposed in the beam path. By means of drive 50 of the stop plate, the desired illumination angle or angles are set by selecting a stop 51 on the stop plate 45.

The illumination field on the mask is adjusted via stop 100. In a first exemplary embodiment, stop 100 is focused on the plane of the mask 145 via drive 101. The size of the stop 100 corresponds to the image field projected onto the detector 200 by the objective 160. In another exemplary embodiment, the intensity distribution of the illumination field is changed by defocusing the image of the stop 100 on the mask 145. In another exemplary embodiment, a stop 100 that is larger than the image field is used. In another exemplary embodiment, the stop 100 is removed from the beam path.

The diffraction pattern of the structure 150 is projected onto the detector 200. This image is focused by moving the mask holder 140 by means of drive 142 toward the optical axis, i.e., in the z-direction. It is sufficient if the precision of focus is approximately within a range of $\Delta z=3$ μm to about 8 μm. The detector 200 configured as a CCD (charge coupled device) chip is read out by means of the data processing system 210 and a digital grayscale image is stored. The performance of the method with a mask inspection microscope employing illuminating radiation in the EUV range with a wavelength of 13.5 nm takes place analogously.

In an exemplary embodiment of the method during the capture of the diffraction pattern a continuous relative movement between mask and detector is carried out. This will be accomplished by the movement of the mask holder 140 by means of drive 142. The mask 145 is moved in a direction perpendicular to the optical axis 1.

The movement of the mask is performed in such a way, that the whole region of the mask to be characterized is scanned. By means of the detector 200 a single diffraction pattern averaged over the whole region to be characterized is scanned.

The speed of movements and the exposure time of the detector 200 has to be specified in a way that each portion of the whole region to be characterized is moved through the beam path during the exposure time, i.e. the region is scanned.

The movement of the mask is for example accomplished line by line. The characterization is started at a corner of the region, the movement is carried out parallel to one first outer edge of the region to be characterized. As soon as the end of the first outer edge will be reached, i.e. as soon as the first line is scanned, the distance of the first outer edge will be increased and the movement will be continued in the opposite direction, that the next line will be scanned.

The region to be characterized may be the whole structured region of the mask or a large connected part to be defined freely.

The control of the scanning movement and the analysis of the diffraction pattern is performed by the data processing system 210.

The angle or angles of illumination and the degree of coherence of the illuminating radiation are adjusted by means of the stops 51, 232 in the pupil plane of the mask inspection microscope and by means of the zoom lens 55.

The angle of the illuminating radiation to optical axis I, the z-axis, is adjusted to the grating period of the to-be-examined structure in such a way that the zeroth and the first (or negative first) diffraction orders are fully contained and resolved in the captured diffraction pattern. The angle of illumination can be adjusted so that higher adjacent diffraction orders, for example the first and second diffraction orders, are imaged in the pupil.

The maximum illumination angle in the z-direction for capturing the zeroth and first diffraction orders is limited by the mask-side numerical aperture $NA_{mask}$ of the objective. The angle (distance in the pupil plane) between the maxima of the zeroth and first diffraction orders is found from the wavelength of the illuminating radiation and the grating period p, in the form $\lambda/p$. Examination is possible only if $\lambda/p<2NA_{mask}$. In order for the first (or negative first) diffraction order to fall within the pupil, the value of the illumination angle in the z-direction must be less than $[\lambda/p-NA_{mask}]$. To obtain a symmetrical arrangement of the maxima of the zeroth and first diffraction orders relative to the center of the pupil plane, the value of the illumination angle in the z-direction must be $\lambda/(2p)$.

In an exemplary embodiment, annular, i.e., ring-shaped, distributions of illumination angles are employed. In this case, the illumination angle to the z-axis is specified, as noted earlier, while the azimuth angle is left undefined. Comparable structures on the mask are thus detected irrespective of their orientation. Examples of stops for practical implementations are given in FIG. 4. A first annular stop 61 has a wide ring, and a second annular stop 62 a narrower ring.

Additional optimized distributions of illumination angles are provided for different structures. Various structures are usually present on a mask. A particularly suitable approach for quality control is to measure the line widths of structures denoted as x- and y-structures, as mentioned above.

For the examination of x-structures, an illumination angle distribution with a pole on the x-axis is provided. The azimuth angle of the incident light is then 0° or 180°. Corresponding stops (x-monopoles) are illustrated in FIG. 4 on stop plate 45 as reference numerals 52 and 53. The degree of coherence of the first x-monopole 52 is greater than the degree of coherence of the second x-monopole 53.

For the examination of y-structures, an illumination angle distribution with a pole on the y-axis is provided. The azimuth angle of the incident light is then 90° or 270°. Corresponding stops (y-monopoles) are illustrated in FIG. 4 on stop plate 45 as reference numerals 56 and 57. The degree of coherence of the first y-monopole 56 is greater than the degree of coherence of the second y-monopole 57.

For the simultaneous examination of x-structures and y-structures, an illumination angle distribution with two poles is provided, designated here as an asymmetric xy-dipole. One pole lies on the x-axis and one pole on the y-axis. Such angles of illumination are obtained, for example, by means of stops where one pole is on the y-axis and one on the x-axis. Examples are illustrated in FIG. 4 as reference numerals 58 and 59.

In a further exemplary embodiment, an illumination angle distribution is used in which a pole lies at the center of the pupil, i.e., the illumination takes place along the optical axis 1. This is advantageous when the zeroth, first and negative first diffraction orders of the illuminating radiation diffracted at the structure are contained in the captured diffraction pattern. For more precise analysis of the diffraction pattern, the intensities of the first and negative first diffraction orders are compared with each other or averaged.

As noted above, captured diffraction patterns are stored as grayscale images in the memory of the data processing system 210. These images are a matrix of 1000×10000 pixels with intensity values ranging from 0 to 255. To determine the intensities of the diffraction maxima, the first step is to identify their respective positions in the diffraction pattern.

If the nominal value of the grating period is known, this and the specified illumination angles can be used to calculate the nominal positions of the to-be-analyzed diffraction maxima of the zeroth and first (or negative first) diffraction orders of the particular structures in the captured diffraction pattern. These calculations and the further analyses are performed in the data processing system 210.

These nominal positions are used to determine the intensities of the diffraction maxima. This is done by adding up all the intensity values of the pixels of the diffraction pattern in a region surrounding the nominal position of a diffraction maximum.

In one exemplary embodiment, the extent of the region of a diffraction maximum is detected by applying a limit value for the intensity values. For instance, only intensity values that are at least 10% of the maximum intensity within the diffraction maximum are taken into account. Alternatively, a fixed limit is set for the intensity.

In a further exemplary embodiment, the position and the region are fixedly specified for each diffraction maximum.

From the intensities of the first and zeroth diffraction maxima, respectively denoted $I_1$ and $I_0$, the quotient $I_1/I_0$ is calculated; this is designated the intensity quotient. In a variant of the method, the reciprocal can also be calculated.

In a further exemplary embodiment, the to-be-measured intensities of the diffraction orders are normalized (clear normalization). A region of the mask that has no structure of any kind is brought into the imaging beam path of the mask inspection microscope. The diffraction pattern captured in this way consists solely of an image of the pole or poles of the stops used. The intensities of these poles, denoted as clear intensities $I_{clear}$, are determined as described above. Intensities measured from diffraction patterns are divided by the clear intensities in order to perform the normalization. The clear intensities for the zeroth and first diffraction orders are: $I_{0clear}=I_0/I_{clear}$; $I_{clear}=I_1/I_{clear}$. The clear-normalized intensity values of the diffraction maxima are calculated, for example, in order to compare the intensity values of the diffraction maxima of different diffraction patterns with one other.

In one exemplary embodiment, in order to calibrate for one or more structures of a mask whose grating periods and line widths are known, a suitable stop is selected and the intensity quotient is determined.

If the grating period is constant, the intensity quotient is, in good approximation, dependent only on line width. Calibration makes it possible to determine the absolute values of the line widths from measurements of the intensity quotients.

The calibration can be performed against absolute measurements performed on the structure on-mask or on-wafer. A scanning electron microscope is used to measure the absolute dimensions of the line width both on the mask and on the wafer.

Since only a slight deviation of line width (i.e., of CD, critical dimension) is to be expected with the masks to be inspected, a linear relationship between the intensity quotients and the line width can be assumed in good approximation.

A nominal value for the critical dimension is usually known for a mask that is to be inspected. For purposes of analyzing the intensity quotients, it can be assumed that this critical dimension approximately corresponds to the mean of the intensity quotients of comparable structures. The relative deviation of the intensity quotients from the mean then corresponds to the relative deviation from the specified critical dimension.

To characterize a mask, a stop is selected that corresponds to the desired distributions of illumination angles—x-monopole, y-monopole, asymmetric xy-dipole or annular—and is adjusted to the grating period of the structure that is to be examined.

To the extent that the positions on a mask of regions containing comparable structures are known, the diffraction patterns are captured specifically at those positions. The respective intensity quotients are calculated directly for all the images. The positions of comparable structures can be determined, for example, from the mask design, i.e., the data relating to the structure represented on the mask.

If the mask design, i.e., the structure represented on the mask, is known, the diffraction patterns of the measured positions can also be simulated. To perform the analysis, the intensity quotients of the measured intensities are compared to those of the simulated intensities. The percentage deviations are represented graphically, as stated above.

In a further measure, for example in cases where the mask design is not specified, positions distributed evenly over the mask are specified for measurement.

All the captured diffraction patterns are searched for diffraction patterns of comparable structures. One criterion is the position of the first diffraction maximum, i.e., its distance from the zeroth diffraction maximum and its azimuth angle. Diffraction maxima of x-structures lie, for example, on the x-axis. A further criterion is the clear-normalized intensities of the diffraction maxima. A further criterion is the spread of the diffraction maxima. A further criterion is the difference from the diffraction patterns simulated on the basis of the mask design. These criteria can be applied individually or in combination.

First, taking all the diffraction patterns into consideration, the clear-normalized intensities of the zeroth and all other diffraction maxima of the diffraction patterns are determined, together with their distances from the zeroth diffraction order. Diffraction patterns whose diffraction maxima are at comparable distances are combined into sets. A tolerance range is defined for the distances within a set. As a further criterion, it is determined whether the clear-normalized intensity values of the respective diffraction orders of different diffraction patterns lie within a defined tolerance range. Diffraction patterns with intensity values outside the tolerance range are not included in the characterization of the mask. An analogous procedure is used for the spatial spread of the diffraction maxima. Diffraction patterns with diffraction maxima whose spread does not lie within a tolerance range are not included in the evaluation.

The intensity quotients are then calculated for each set of diffraction patterns, as described above.

For the analysis, the mean of all the intensity values is calculated, together with the percentage deviation of all the values from this mean. Different percentage deviations are assigned different colors or color shades. The measurement values are then represented by the respective color in a two-dimensional diagram of the mask. To the extent that the intensity quotients have been calibrated against known CD values as noted above, the absolute CD values can be given in the two-dimensional diagram.

A further exemplary embodiment is used for masks with numerous regions containing identical structures, so-called dies. To increase the precision, the mean of the intensity quotients of identical positions on all the dies is measured. For the analysis, the percentage deviation of the individual intensity quotients from the mean across all the dies is then given for each position.

Figure 6:
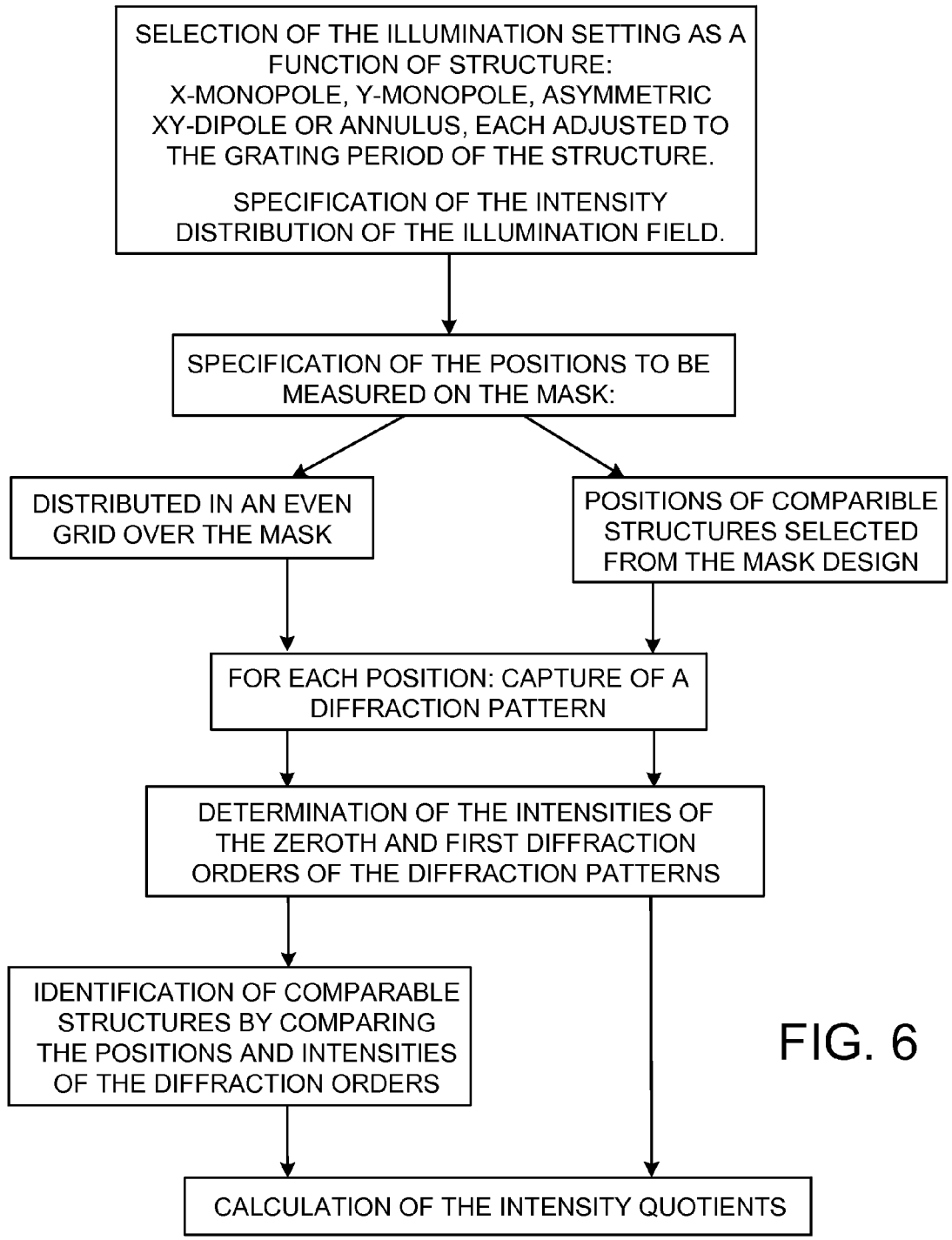
FIG. 6: a flow chart of an example of the method according to the invention.

An overview of the method according to the invention is provided in FIG. 6. Referring to FIG. 6, the method includes selecting the illumination setting as a function of structure:

x-monopole, y-monopole, asymmetric xy-dipole or annulus, each adjusted to the grating period of the structure, and specify the intensity distribution of the illumination field. The method includes specifying the positions to be measured on the mask, in which the positions can be distributed in an even grid over the mask or positions of comparable structures can be selected from the mask design. If the positions are distributed in an even grid over the mask, the following are performed: for each position, capturing a diffraction pattern; determining the intensities of the zeroth and first diffraction orders of the diffraction patterns; and identifying comparable structures by comparing the positions and intensities of the diffraction orders. If positions of comparable structures are selected from the mask design, the following are performed: for each position, capturing a diffraction pattern; and determining the intensities of the zeroth and first diffraction orders of the diffraction patterns. The method further includes calculating the intensity quotients.

The invention claimed is:

1. A method for characterizing a mask having a structure, comprising:
    illuminating said mask under at least one illumination angle with monochromatic illuminating radiation, so as to produce a diffraction pattern of said structure that includes at least two maxima of adjacent diffraction orders,
    capturing said diffraction pattern,
    determining the intensities of the maxima of the adjacent diffraction orders, and
    determining an intensity quotient of the intensities;
    wherein said diffraction pattern is projected entirely onto a single detector in order to be captured, said diffraction pattern is being captured during a continuous relative movement between said mask and said detector, and the mask is moved relative to an optical axis during capture of the diffraction pattern.

2. The method as in claim 1, comprising:
    determining a line width of said structure from at least one correlation between at least one determined intensity quotient of a structure and a known line width of said structure.

3. The method as in claim 1, wherein said illuminating radiation generates on said mask an illumination field having a main region and an edge region, said edge region surrounding said main region, wherein the intensity of said illuminating radiation is constant in said main region but decreases continuously in said edge region.

4. The method as in claim 3, wherein the decrease in intensity in said edge region corresponds to a Gaussian function.

5. The method as in claim 1, wherein said illumination field on said mask is defined by means of a field stop and the intensity distribution of said illumination field is adjusted by defocusing said field stop.

6. The method as in claim 1, wherein said at least one illumination angle is adjusted to a grating period of said structure.

7. The method as in claim 1, wherein said at least one illumination angle is adjusted to an orientation of the grating period of said structure on said mask.

8. The method as in claim 1, wherein said structure on said mask is illuminated simultaneously under at least two illumination angles, each of said illumination angles being adjusted to the orientation of the grating periods of different structures on said mask.

9. The method as in claim 1, wherein said at least one illumination angle is predefined by arranging a stop in a pupil plane of an illumination beam path of a mask inspection microscope.

10. The method as in claim 9, wherein said stop is configured as an annulus that is adjusted to the grating periods of different structures on said mask.

11. The method as in claim 9, wherein said stop is configured as a monopole, the position of the pole being adapted to the orientation of the grating period of a structure on said mask.

12. The method as in claim 9, wherein said stop is configured as an asymmetric dipole, the positions of the two poles being adapted to the orientations of the grating periods of different structures on said mask.

13. The method as in claim 1, wherein the intensities of the adjacent diffraction orders are normalized to a reference value, particularly to the intensity, measured during the characterization of a mask with no structure.

14. The method as in claim 1, wherein a further characterization of the structure is performed by applying at least one of the criteria: position of the diffraction order maxima, spacing between the diffraction order maxima, intensities of the diffraction order maxima, or spread of the diffraction order maxima.

15. The method as in claim 1, wherein a further characterization of the structure is performed by comparing the captured diffraction pattern to a simulated diffraction pattern.

16. The method as in claim 1, comprising specifying plural positions on the mask at which structures will be characterized.

17. The method as in claim 16, wherein positions that are evenly distributed over the surface of the mask are specified.

18. The method as in claim 16, wherein comparable structures are identified in the diffraction patterns by applying at least one of the following criteria: positions of the diffraction order maxima, spacing of the diffraction order maxima, intensities of the diffraction order maxima, or spread of the diffraction order maxima.

19. The method as in claim 15, wherein positions at which comparable structures are formed on the mask are specified.

20. The method as in claim 19, wherein the mean of the intensity quotients of all comparable structures and the percentage deviation of the individual intensity quotients from the mean are calculated.

21. A mask inspection microscope comprising a data processing system, in which the mask inspection microscope performs the steps according to the method as set forth in claim 1.

22. The method of claim 1 in which the mask is moved in a direction perpendicular to the optical axis during capture of the diffraction pattern.

23. The method of claim 1 in which only a portion of the mask is illuminated at any given time during capture of the diffraction pattern.

* * * * *

UNITED STATES PATENT AND TRADEMARK OFFICE
CERTIFICATE OF CORRECTION

| | | |
|---|---|---|
| PATENT NO. | : 9,213,003 B2 | Page 1 of 1 |
| APPLICATION NO. | : 13/995250 | |
| DATED | : December 15, 2015 | |
| INVENTOR(S) | : Sascha Perlitz | |

It is certified that error appears in the above-identified patent and that said Letters Patent is hereby corrected as shown below:

IN THE SPECIFICATION

Column 8

Line 23, delete "reading" and insert -- being read --

Line 34, delete "illumination" and insert -- illuminating --

Line 41, delete "for" and insert -- to --

Line 42, delete "232," and insert -- 232, which --

Line 44, delete "on the" and insert -- on --

Column 11

Line 35, delete "$I_{clear}$" and insert -- $I_{1clear}$ --

Signed and Sealed this
Eighth Day of March, 2016

Michelle K. Lee
*Director of the United States Patent and Trademark Office*